United States Patent
Masada et al.

(10) Patent No.: US 8,029,609 B2
(45) Date of Patent: Oct. 4, 2011

(54) EJECTION LIQUID, EJECTION DEVICE, EJECTION CARTRIDGE, AND METHOD OF MAKING DROPLETS FROM LIQUID

(75) Inventors: Yohei Masada, Tokyo (JP); Masaru Sugita, Tokyo (JP); Hideki Kaneko, Yokohama (JP); Takeshi Miyazaki, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 679 days.

(21) Appl. No.: 11/570,744

(22) PCT Filed: Sep. 27, 2005

(86) PCT No.: PCT/JP2005/018247

§ 371 (c)(1),
(2), (4) Date: Dec. 15, 2006

(87) PCT Pub. No.: WO2006/035977

PCT Pub. Date: Apr. 6, 2006

(65) Prior Publication Data

US 2007/0222842 A1    Sep. 27, 2007

(30) Foreign Application Priority Data

Sep. 27, 2004 (JP) ................................. 2004-279864
Aug. 31, 2005 (JP) ................................. 2005-252154

(51) Int. Cl.
*B41J 2/175* (2006.01)
*C09D 11/04* (2006.01)
(52) U.S. Cl. ..................................... 106/31.13; 347/87
(58) Field of Classification Search ...................... 106/31
See application file for complete search history.

(56) References Cited

U.S. PATENT DOCUMENTS

| | | | |
|---|---|---|---|
| 5,679,143 A * | 10/1997 | Looman | 106/31.43 |
| 5,894,841 A | 4/1999 | Voges | 128/203.12 |
| 6,100,315 A * | 8/2000 | Kitamura et al. | 523/160 |
| 6,120,761 A | 9/2000 | Yamazaki et al. | 424/85.1 |
| 6,277,367 B1 | 8/2001 | Yamazaki et al. | 424/85.1 |
| 6,525,102 B1 | 2/2003 | Chen et al. | 514/970 |

(Continued)

FOREIGN PATENT DOCUMENTS

EP        1 314 437 A1    5/2003
(Continued)

OTHER PUBLICATIONS

Allain et al., "Microarray sampling-platform fabrication using bubble-jet technology for a biochip system," Fresenius J. Anal. Chem., vol. 371, 2001, pp. 146-150.

(Continued)

*Primary Examiner* — Melvin Mayes
*Assistant Examiner* — Yun Qian
(74) *Attorney, Agent, or Firm* — Fitzpatrick, Cella, Harper & Scinto

(57) ABSTRACT

An ejection liquid which can be ejected stably by an inkjet method using thermal energy even in the case of containing at least one of proteins and peptides, and a method and device of discharging a liquid containing at least one of proteins and peptides, which use the ejection liquid. At least one compound having a guanidine group is added to an aqueous solution of at least one of proteins and peptides to improve its qualifications to an ejection event by an inkjet method using thermal energy.

3 Claims, 7 Drawing Sheets

U.S. PATENT DOCUMENTS

| | | | |
|---|---|---|---|
| 6,548,020 B2 | 4/2003 | Okamoto et al. | 422/68.1 |
| 6,569,406 B2 | 5/2003 | Stevenson et al. | 424/43 |
| 6,627,187 B2 | 9/2003 | Yamazaki et al. | 424/85.1 |
| 6,838,975 B2 | 1/2005 | Litwiller et al. | 340/5.67 |
| 6,921,433 B2 | 7/2005 | Kuribayashi et al. | 106/499 |
| 6,926,392 B2 | 8/2005 | Sasaki et al. | 347/65 |
| 6,964,700 B2 | 11/2005 | Uji et al. | 106/31.28 |
| 7,011,825 B2 | 3/2006 | Yamazaki et al. | 424/85.1 |
| 7,030,086 B2 | 4/2006 | Chen et al. | 514/12 |
| 7,083,667 B2 | 8/2006 | Murai et al. | 106/31.43 |
| 7,202,065 B2 | 4/2007 | Römisch et al. | 435/183 |
| 2002/0092519 A1 | 7/2002 | Davis | 128/200.14 |
| 2002/0110552 A1 | 8/2002 | Römisch et al. | 424/94.63 |
| 2002/0177221 A1 | 11/2002 | Nishiguchi et al. | 435/287.2 |
| 2003/0064052 A1* | 4/2003 | Waters et al. | 424/85.2 |
| 2003/0119179 A1 | 6/2003 | Okamoto et al. | 435/287.2 |
| 2003/0190316 A1* | 10/2003 | Kakuta et al. | 424/132.1 |
| 2004/0037803 A1 | 2/2004 | Sato | 424/85.1 |
| 2004/0259083 A1 | 12/2004 | Oshima | 435/6 |
| 2005/0188894 A1 | 9/2005 | Yamagishi et al. | 106/31.43 |
| 2006/0093576 A1 | 5/2006 | Chen et al. | 424/85.2 |
| 2006/0093598 A1 | 5/2006 | Chen et al. | 424/94.2 |
| 2006/0183046 A1 | 8/2006 | Murai et al. | 430/108.2 |
| 2007/0206081 A1 | 9/2007 | Masada et al. | 347/100 |
| 2007/0221215 A1 | 9/2007 | Sugita et al. | 128/203.12 |
| 2007/0277701 A1 | 12/2007 | Toyoda et al. | 106/31.48 |

FOREIGN PATENT DOCUMENTS

| | | | |
|---|---|---|---|
| JP | 7-173073 A | 7/1995 | |
| JP | 2002-148259 A | 5/2002 | |
| JP | 2002/248171 A | 9/2002 | |
| JP | 2002-249441 A | 9/2002 | |
| JP | 2002/355025 A | 12/2002 | |
| JP | 2003/510368 A | 3/2003 | |
| JP | 2003/154655 A | 5/2003 | |
| JP | 2003/154665 A | 5/2003 | |
| JP | 2004-515467 | 5/2004 | |
| JP | 2004-196824 A | 7/2004 | |
| JP | 2004-532861 A | 10/2004 | |
| JP | 3610231 | 1/2005 | |
| JP | 3618633 | 2/2005 | |
| WO | WO 01/24814 A1 | 4/2001 | |
| WO | WO 02/11695 A2 | 2/2002 | |
| WO | WO 02/13860 A1 | 2/2002 | |
| WO | WO 02/17957 A1 | 3/2002 | |
| WO | WO 02/092813 A1 | 11/2002 | |
| WO | WO 02/094342 A2 | 11/2002 | |

OTHER PUBLICATIONS

Howard et al., "Ink-Jet Printer Heads for Ultra-Small-Drop Protein Crystallography," BioTechniques, vol. 33, No. 6, Dec. 2002, pp. 1302-1306.

Mar. 26, 2008 Japanese Official Action in Japanese Patent Appln. No. 2005-252154 (with translation).

Motonori Kudo, et al., "Control of Suppression/Promotion of Aggregation by Addition of Small Molecule", Summary Collection of Japan Society for Bioscience, Biotechnology and Agrochemistry Convention, 2002, vol. 2002, 216.

Kentaro Shiraki, "Small Molecule Additive for Suppressing Deactivation and Agglomeration of Protein", Biophysics, 2004, vol. 44, No. 2, pp. 87-90.

Dec. 6, 2005 International Search Report and Written Opinion in Intl. Appln. No. PCT/JP2005/018247.

* cited by examiner

EJECTION LIQUID, EJECTION DEVICE, EJECTION CARTRIDGE, AND METHOD OF MAKING DROPLETS FROM LIQUID

TECHNICAL FIELD

The present invention relates to: a liquid composition suitable for making droplets from a liquid containing at least one of proteins and peptides and a method of making such droplets; and an ejection device using such a method of making the liquid droplet.

BACKGROUND ART

Currently, many attempts have been conducted to utilize a protein solution as liquid droplets. For example, for the drug delivery method, the liquid droplets have been considered to be applied in transmucosal administration because of, for example, advantages in that only a small amount of protein may be required in the production of a biochip or biosensor and the protein may be integrated easily. In addition, attentions have been paid to a method of using a fine liquid droplet of protein for control on crystallization of protein and also for screening of a physiologically active substance (see, for example, Japanese Patent Application Laid-Open No. 2002-355025, Allain L R et al., "Fresenius J. Anal. Chem", vol. 371, p. 146-150, 2001, and Howard E I and Cachau R E, "Biotechniques", vol. 33, p. 1302-1306, 2002).

In recent years, mass production of proteins, particularly useful proteins such as enzymes and those having physiological activities has become possible by any technology such as genetic recombinant technology. Therefore, the process of making protein into liquid droplets can be an effective means in the field of searching, utilizing, and applying a novel protein medicine. More specifically, there are increasing significant demands on means for providing patients with many pharmaceutical agents by microdroplets. In particular, microdroplets have become important for the administration of proteins, peptides, and other biological materials from the lungs. In other words, the lungs have been remarked as an administration route in place of an injection of a macromolecule peptide-based drug represented by insulin because the lungs have lung alveolis with their own extensive surface areas of 50 to 140 $m^2$ and the epithelium provided as a barrier of absorption is as thin as 0.1 μm, while the enzyme activities of the lungs are smaller than those of the gastrointestinal tract.

In general, the deposition of microdroplets of drug in the lungs has been known to depend largely on the mass median aerodynamic diameters thereof. In particular, the delivery of the microdroplets to the lung alveolis in the deep portions of the lungs essentially requires the development of: a stable pharmaceutical preparation which can be given with high reproducibility for a narrow particle size distribution of 1-5 μm of the droplets; and an administration form.

As a method of preparing uniform droplets with a narrow particle size distribution, the use of a suitable droplet generator diverted from those used in inkjet printing in the production of extremely fine droplets and the application of the droplets have been reported in the art (see, for example, U.S. Pat. No. 5,894,841 and Japanese Patent Application Laid-Open No. 2002-248171). Here, the specific inkjet printing method concerned involves leading liquid to be ejected into a small chamber where the liquid is subjected to an ejection pressure, thereby allowing droplets of the liquid to be ejected from orifices. A discharging method may be any one of those known in the art, such as one that generates air bubbles spouting droplets through orifices formed on a chamber by means of thermal transducers such as thin-film resistors (i.e., a thermal inkjet method) and one that ejects liquid directly from orifices formed on a chamber by means of piezoelectric transducers (i.e., a piezo inkjet method). The chamber and the orifices are incorporated in a print head element and the element is then connected to both a liquid-supplying source and a controller for controlling the ejection of droplets of the liquid.

For allowing the lungs to absorb a drug, the dose of the drug should be controlled. Therefore, making droplets from the liquid by the inkjet method, which is capable of adjusting the ejection amount thereof, is a very preferable configuration. On the other hand, however, the ejection of a solution should be surely carried out in this case. However, the ejection of a protein solution is unstable when the protein solution is only controlled with respect to its surface tension and coefficient of viscosity. Therefore, the difficulty in quantitative ejection has often occurred.

Problems associated with the process of making droplets of a protein or peptide using the inkjet method are due to the fact that the tertiary structure of the protein is brittle. Thus, the aggregation or degradation of the protein may occur when the configuration thereof is destroyed. When the process of making droplets is carried out using the inkjet method, the structures of many proteins may become unstable owing to physical stress such as pressure or shearing stress or to high surface energy peculiar to microdroplets (if the thermal inkjet method is employed, heat is further applied in addition to the above stress). In particular, in the case of the inkjet method, those physical actions are extremely larger than the shearing force and thermal energy to be applied by conventional stifling or heat treatment (for example, in the case of the thermal inkjet method, approximately 300° C. and 90 atm are applied momentarily). Furthermore, several physical stresses are impressed at the same time, so that the stability of protein may tend to be substantially lowered, compared with the case of usually handling the protein. On this account, the conventional technology for stabilizing protein may be insufficient when the inkjet technology is employed. If such a problem occurs, the protein may be aggregated at the time of making droplets and nozzles may be then clogged, thereby making it difficult to eject droplets.

Furthermore, droplets having diameters of 1 to 5 μm, which are suitable for the inhalation into the lungs, are extremely smaller than those having diameters of approximately 16 μm used in any printer commercially available at present. Therefore, a larger surface energy or shearing stress may be impressed on the droplets than on the droplets used in the printer. Therefore, it is more difficult to eject microdroplets suitable for inhaling protein into the lungs.

In consideration of the diameters of the droplets as described above, a thermal inkjet method capable of having highly-densified nozzles and a low production cost is preferably used as a method of discharging a protein solution.

In the pamphlet of International Publication No. WO 02/094342, there is disclosed a compound for regulating surface tension and a method of adding a humectant for a liquid composition for the pulmonary absorption of a droplet prepared using a thermal inkjet method. Here, for increasing the stability of protein in a solution provided as droplets by the surface tension, viscosity, or moisturizing action of the solution, a surfactant or a water-soluble polymer such as polyethylene glycol is added.

However, there is no description about the stability of discharging, and also the addition of a surfactant or a water-soluble polymer exerts insufficient effects when the concentration of protein or peptide increases. As a result, the additive itself often blocks the stability of discharging. In addition, there are more surfactants which have been recognized as of no effect at all than those having effects. Besides, the stability is defined by not only the surface tension and viscosity. Therefore, the method disclosed in the document is not a common practice for the stabilization of ejection. Therefore, for actual use, any liquid to be used for an ejection purpose, which is capable of discharging protein or peptide in a stable manner, becomes essential.

In addition, each of Japanese Patent Application Laid-Open No. 2003-154655 and Japanese Patent No. 03610231 discloses a method of preparing a protein chip or the like as a method of utilizing a protein or peptide such that it is ejected by a thermal inkjet method. However, there was no substantial description about stable ejection of the protein and peptide.

As described above, the inkjet method has been known in the art as one of the methods of discharging a liquid sample after making it into fine droplets. The inkjet method has a characteristic feature of showing high controllability for the amount of liquid to be ejected after being provided as droplets even if the amount is extremely small. Methods of discharging microdroplets based on the inkjet method include a vibration method using a piezoelectric element or the like and a thermal inkjet method using a microheater element. In the case of the vibration method using the piezoelectric element or the like, reducing the size of a piezoelectric element to be used is limited and the number of ejection orifices formed per unit area is also restricted. Besides, production costs increase as the number of ejection orifices per unit area increases. In contrast, in the case of the thermal inkjet method, the size of the microheater element can be comparatively easily reduced, and also the number of ejection orifices formed per unit area can be larger than that of the vibration method using a piezoelectric element or the like, while the production costs thereof can be also significantly reduced.

When the thermal inkjet method is applied, for controlling the state of appropriate aerosol of microdroplets of liquid to be ejected from respective orifices and the amount of the liquid, there is a need of coordinating the physical properties of the liquid to be ejected. In other words, the composition of the liquid, including the kind and composition of a solvent and the concentration of a solute, the solvent and the solute being contained in the sample of liquid to be ejected, should be schemed so as to be adjusted to obtain a desired volume of the microdroplet. Furthermore, various kinds of mechanisms for discharging droplets on the basis of the principle of the thermal inkjet method have been also developed. Concretely, for a conventional inkjet head to be mounted on a printer, the amount of each liquid droplet to be ejected is on the order of several pico-liters. While technologies of an ejection mechanism and an ejection method, which allow droplets to be formed as those having extremely small sizes in the order of several sub-pico liters or femto-liters, have been developed (see the pamphlet of International Publication No. WO 02/092813). For instance, when somatic cells of several micrometers in size are provided as a target to be coated with a drug, it is assumed that using the extremely fine droplets as individual droplets to be ejected may be requested.

There is known, as a method of stabilizing protein, a method involving adding any one of water-soluble polymers such as surfactants, glycerols, various kinds of hydrocarbons, and polyethylene glycols as well as albumin. Also, there are known, as methods of preserving a protein preparation for a long term, several methods (Japanese Patent No. 03618633, International Publication No. WO 02/017957, and National Publication No. of the translated version of PCT application 2003-510368), where amino acids are added to erythropoietin, G-CSF, and interferon. However, according to the study conducted by the inventors of the present invention, on the basis of the kind and concentration of protein or peptide or the concentration of an additive, those methods may be insufficient for the stability of ejection in the thermal inkjet method.

In many cases, there is substantially no effect on an improvement in ejection performance when protein or peptide is ejected even after formulation with polyols such as ethylene glycol and glycerin, and a humectant such as urea, which are suitable additives for ink to be used in inkjet printing. Therefore, it has been demanded to develop an ejection liquid to stably eject a protein or peptide solution on the basis of the principle of the inkjet method using thermal energy.

DISCLOSURE OF THE INVENTION

The present invention aims to provide: a liquid composition as an ejection liquid to be provided for stably discharging droplets containing at least one of proteins and peptides by means of an inkjet method on the basis of the principle of the inkjet method using thermal energy; and an ejection method and ejection device suitable for the use of protein droplets.

The ejection liquid of the present invention is an ejection liquid to be ejected from an orifice using thermal energy for ejection, containing: at least one selected from proteins and peptides; a compound having a guanidine group; and a liquid medium.

A cartridge for ejection liquid of the present invention contains: a tank in which the ejection liquid is reserved; and a thermal inkjet head.

A liquid inhaler of the present invention contains the cartridge described above and an ejection orifice for introducing a liquid to be ejected from a liquid-discharging part of a thermal inkjet head of the cartridge into an inhalation part of a user.

A method of making droplets from liquid of the present invention includes applying thermal energy to a liquid containing at least one of proteins and peptides to provide the liquid as droplets, and is characterized in that the liquid contains a compound having a guanidine group.

According to the present invention, the compound containing a guanidine group is added to the solution containing at least one of proteins and peptides, so that an ejection liquid capable of being ejected stably in the method of making droplets from the liquid by applying thermal energy thereto. In addition, the addition of a surfactant to the ejection liquid may cause a synergistic effect with respect to the stability of ejection, thereby allowing the ejection of the protein solution in higher concentration. When at least one of the proteins and peptides is a therapeutic component, the ejection liquid may be provided as droplets by discharging from a portable ejection device, so that the at least one of proteins and peptides provided as a therapeutic component to be effective in the lung when it is inhaled can be inhaled from the lungs. In addition, the ejection liquid can be used for the production of a biochip and biosensor, sensing, and screening of a biological substance, when it is ejected on a substrate.

BRIEF DESCRIPTION OF THE DRAWINGS

FIG. 1 is a schematic diagram for illustrating a method of discharging a protein on a substrate.

FIG. 2 is an illustration of one pattern for arranging a protein on a substrate.

FIG. 3 is a schematic diagram for illustrating an inhalation head cartridge unit.

FIG. 4 is a perspective diagram of an inhaler.

BEST MODE FOR CARRYING OUT THE INVENTION

Figure 1:
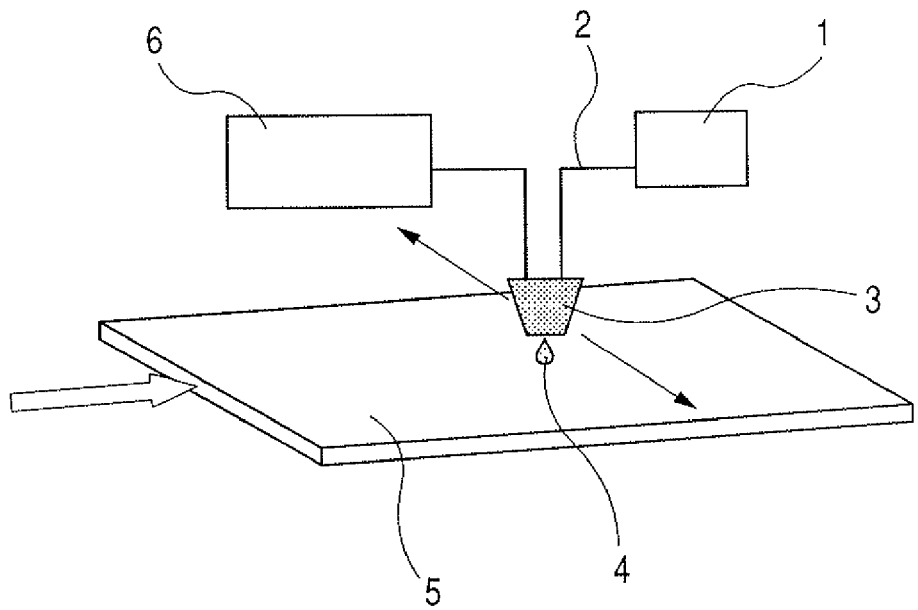

The term "protein(s)" as used in the present invention refers to any polypeptide in which a number of amino acids are linked with each other by peptide linkages and which is dissolved or dispersed in an aqueous solution. In addition, the term "peptide(s)" as used in the present invention refers to a peptide in which two or more and 50 or less amino acids are being linked with each other by peptide linkages. Those proteins and peptides may be chemically synthesized or may be purified from those naturally occurred. Typically, they may be recombinants of native proteins and peptides. In general, the proteins and peptides can be chemically modified by covalently bonding amino acid residues to protein and peptide molecules, so that their therapeutic effects may be prolonged to attain improvements in their effects. When the present invention is implemented, various kinds of proteins and peptides which are desired to be provided as droplets can be used. The proteins and peptides which can be used in the present invention are not specifically limited as far as they have physiological activities on the living bodies and retain their activities in the living bodies. Most typically, making the droplets from the proteins and peptides of the present invention is for the delivery of proteins and peptides which are useful for therapeutics to the lungs. Examples thereof include: calcitonins; blood coagulation factors; various hemopoietic factors such as G-CSF, GM-CSF, SCF, EPO, GM-MSF, and CSF-1; interleukins such as IL-1, IL-2, IL-3, IL-4, IL-5, IL-6, IL-7, IL-8, IL-9, IL-10, IL-11, and IL-12; IGFs; and cytokines such as M-CSF, thymosin, TNF, and LIF. Proteins having other useful therapeutic effects include vasoactive peptides, interferons (alpha, beta, gamma, and common interferon), growth factors and hormones such as human growth hormones and other animal growth hormones such as bovine, hog, and avian growth hormones, insulin, oxytocin, angiotensin, methionine-enkephalin, substance P, ET-1, FGF, KGF, EGF, IGF, PDGF, LHRH, GHRH, FSH, DDAVP, PTH, vasopression, glucagon, and somatostatin. Protease inhibitors may be also used, including leupeptin, pepstatin, and metalloproteinase inhibitors such as TIMP-1 and TIMP-2. Nerve growth factors such as BDNF and NT3 may be also used. In addition, plasminogen activators such as tPA, urokinase, and streptokinase may be also used Any peptide moiety, which contains all or part of the main structure of a parent protein and retains at least a part of biological characteristics of the parent protein, may be also used. Any of the above substances modified with analogs, such as substituted or defective analogs, modified amino acids such as peptide analogs, and water-soluble polymers such as PEG and PVA may be also used.

Furthermore, for the production of a biochip or biosensor and the use for screening proteins and peptides, in addition to the above proteins and peptides, the above substances modified with any of various enzymes such as oxidase, reductase, transferase, hydrase, lyase, isomerase, synthetase, epimerase, mutase, and rasease, various antibodies such as IgG and IgE, and antigens thereof, and proteins and peptides for diagnostic use, such as allergen, chaperoning avidin, and biotin, and immobilizing agents may be also used.

Any protein or peptide in the ejection liquid may be one having a molecular weight ranging from 0.3 k to 150 kDa. The content of at least one selected from proteins and peptides, which is selected depending on purposes, ranges preferably from 1 μg/ml to 200 mg/ml, more preferably from 0.1 mg/ml to 60 mg/ml.

In general, it is known that the ejection of ink by the inkjet method may be improved by the addition of a surfactant or a solvent such as polyethylene glycol. However, the inventors have found that when the protein or peptide solution is ejected, an improvement in ejection ability cannot be recognized only by the addition and an additional additive may be required.

In the following description, the present invention will be described mainly with respect to a configuration using the thermal inkjet method because the thermal inkjet method shows the most significant improvement in ejection ability. When the thermal inkjet method is employed, a small-sized device capable of attaining lower production costs and higher densified ejection nozzles, while requiring frequent replacement of a head with new one has been demanded. Under such circumstances as described above in which the present invention is used frequently, the thermal inkjet method can be preferably used. As a result of concentrated study, the inventors of the present invention have found that a protein or peptide solution added with a compound having a guanidine group is suitable for stably making droplets using the inkjet method.

The compound having a guanidine group may contribute to the stability of ejection. The reason thereof has not been revealed, but is considered to be follows.

A guanidine group has a planar structure on which an amino group moiety acts a hydrogen donator to form a hydrogen bond and the upper and lower surfaces of the plane of the molecule are covered with n electrons while having hydrophobicity. In addition, the peptide bonding between proteins or peptides may be of no substantial difference between these bonds even in the case of a hydrogen bond with a guanidine group or a hydrogen bond as a linkage between water and peptide. Furthermore, as the guanidine group has a hydrophobic moiety, the hydrophobic moiety of the guanidine group and the hydrophobic moiety of the protein or peptide may act with each other while the amino group moiety forms a hydrogen bond with water, thereby causing an increase in the water-solubility of the denatured protein or peptide to inhibit the action between the proteins or peptides. Such an action may prevent the denature and aggregation of protein or peptide caused by energy generated at the time of discharging with the thermal inkjet method, thereby stabilizing the ejection.

The study conducted by the inventors of the present invention has confirmed that when the thermal inkjet method allows the protein or peptide to be ejected in a concentration enough to show effective bioactivity, almost no ejection can be observed if the molecular weight thereof is 3,000 or more at an ejection frequency of 20 kHz, although this phenomenon depends on the type or concentration of the protein or peptide.

When the present invention is performed, a thermal inkjet head is preferably driven at a low driving frequency. The reason of different ejection stabilities depending on the driving frequencies is that an ejection liquid may be heated by heaters in the thermal inkjet head and then part of protein or peptide may become insoluble in water to prevent the energy transfer from the heater to the solution. When the driving frequency is low, even if insoluble substances may be temporarily generated, they will be re-dissolved with the time period up to the subsequent driving. On the other hand, when the driving frequency is high, the recovery of solubility may be insufficient and, as a result, the stability of ejection may decrease. However, for allowing the ejection of a large amount of the solution, the ejection should be carried out in high frequency at a certain level or more. In the present invention, therefore, the driving frequency is preferably in the range of 0.1 kHz to 100 kHz, more preferably in the range of 1 kHz to 30 kHz.

The compound having a guanidine group used in the present invention is preferably any one of those each represented by the following general formula (1).

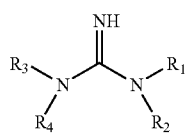

(1)

In the formula (1), each of $R_1$-$R_4$ is not specifically limited as far as it constitutes any combination of groups that provides a structure capable of allowing the compound to retain its solubility to water, preferably each of $R_1$-$R_4$ is independently a hydrogen atom, a polar functional group, a hydrocarbon group, or an acyl group. Examples of suitable polar functional groups include an amino group, a hydroxyl group, a carboxyl group, a sulfonic group, an aldehyde group, and a nitro group. The number of carbons in the hydrocarbon group is not specifically limited as far as it is not less than 1, and is preferably 1 to 18. Examples of suitable hydrocarbon groups include methyl, ethyl, propyl, isopropyl, n-butyl, isobutyl, tert-butyl, n-pentyl, neopentyl, n-hexyl, isohexyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl, vinyl, allyl, cyclopentyl, cyclohexyl, oleyl, linoleyl, linolenyl, and phenyl groups. Each of the hydrocarbon groups may be substituted with at least one of a halogen atom, an acyl group, and a polar functional group, or may have an unsaturated bond therein. In addition, each of the hydrocarbon groups may contain at least one of an ether bond, an ester bond, and an amide bond therein. Furthermore, salts of those compounds may be used. Furthermore, a polymer in which each of those compounds may be provided as a single unit of the polymer may be used, and a surfactant containing any one of those compounds in its structure may be used. The compound having a guanidine group is preferably 59-1,000, more preferably 59-300 in molecular weight. The compound is preferably a compound having a solubility to water larger than 0.01% by weight at a neutral region (pH 5.5-8.5).

Of the compounds each having a guanidine group, preferable compounds include arginine derivatives each represented by the general formula (2) described below. Arginine is useful as an additive because it is one of the amino acids and a derivative thereof has a little effect on the living body.

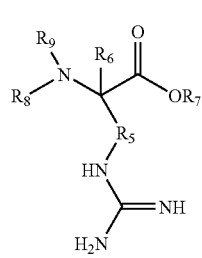

(2)

$R_5$-$R_9$ may form any combination as far as the solubility to water can be retained. $R_5$ is a straight hydrocarbon having 1-6 carbon atoms, where the hydrocarbon may be saturated or unsaturated.

Each of $R_6$-$R_9$ is independently a hydrogen atom, a hydrocarbon group, or an acyl group. Each of them may contain an ether bond, an ester bond, or an amide bound therein. The number of carbons in the hydrocarbon group is not specifically limited as far as it is not less than 1, and is preferably 1 to 18. Examples of suitable hydrocarbon groups include methyl, ethyl, propyl, isopropyl, n-butyl, isobutyl, tert-butyl, n-pentyl, neopentyl, n-hexyl, isohexyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl, vinyl, allyl, cyclopentyl, cyclohexyl, oleyl, linoleyl, linolenyl, and phenyl groups.

The number of carbons in the carbon chain of the acyl group is not specifically limited as far as it is not less than 1, and is preferably 1 to 18. Examples of a suitable acyl group include formyl, acetyl, propionyl, butyryl, valeryl, oxalyl, malonyl, succinyl, benzoyl, acryloyl, methacryloyl, crotonyl, caproyl, capryloyl, lauroyl, myristoyl, palmitoyl, stearoyl, and oleoyl groups.

Furthermore, each of those hydrocarbon groups $R_5$-$R_9$ may be substituted with at least one functional group selected from a halogen atom, an acyl group, a hydroxyl group, a carboxyl group, a sulfonic group, an aldehyde group, an amide group, an amino group, and a nitro group, or may contain at least one of an ether bond, an ester bond, and an amide bond therein.

The halogen atom may be any one of fluorine, chlorine, bromine, and iodine atoms. Part or whole of the hydrogen atoms constituting the hydroxyl group, carboxyl group, amide group, and amino group may be substituted with hydrocarbon groups.

In addition, salts of the compounds each represented by the formula (2) may be used. Furthermore, a polymer in which each of those compounds may be provided as a single unit of the polymer may be used, and a surfactant containing any one of those compounds in its structure may be used.

Of the arginine derivatives, more preferable compounds include arginine, arginine methylester, arginine ethylester, Nα-acyl arginine and salts thereof, and most preferable compounds include arginine, Nα-acyl arginine, and salts thereof.

The addition concentration of the compound having a guanidine group is preferably 0.01 to 30% by weight, more preferably 1 to 20% by weight, although it depends on the type and concentration of protein or peptide.

In the present invention, it is found that the stable ejection can be retained by co-addition of the compound having a guanidine group and the surfactant even if the concentrations of the additives are substantially reduced. The addition amount of the compound having a guanidine group can be one-half to one-tenth of a solution having the same protein concentration by the addition of 0.2 to 1 part by weight of the surfactant with respect to one part by weight of the compound having a guanidine group. The effects of the surfactant are different from those of the compound having a guanidine group and may include the action of preventing a protein from being denatured and the action of redissolving the aggregated protein to stabilize the ejection. A combination of those two different effects may lead to a synergistic effect to substantially improve the stability of ejection. The stability of ejection may not be secured because the surfactant cannot solely prevent the aggregation of protein completely because of poor levels of those actions.

The term "surfactant" as used in the present invention refers to a compound having both a polar moiety and a non-polar moiety in one molecule and also having a characteristic feature in that the moieties are on their respective different local areas on the molecule, the surfactant reduces two surface tensions in immiscible correlation by means of a molecular arrangement on the interface, and a micell can be formed.

Specifically, typical examples of the surfactant to be used, but not limited to, include: a sorbitan fatty acid ester such as sorbitan monocaprylate, sorbitan monolaurate, or sorbitan monopalmitate; an N-acylamino acid of a surfactant having an amino acid as a hydrophilic group such as N-coconut oil fatty acid glycine, N-coconut oil fatty glutamic acid, or N-lauroyl glutamic acid; a fatty acid salt of amino acid; a glycerin fatty acid ester such as glycerin monocaprylate, glycerin monomyristate, or glycerin monostearate; a polyglycerin fatty acid ester such as decaglyceryl monostearate, decaglyceryl distearate, or decaglyceryl monolinolate; a polyoxyethylene sorbitan fatty acid ester such as polyoxyethylene sorbitan monolaurate, polyoxyethylene sorbitan monooleate, polyoxyethylene sorbitan monostearate, polyoxyethylene sorbitan monopalmitate, polyoxyethylene sorbitan trioleate, or polyoxyethylene sorbitan tristearate; a polyoxyethylene sorbitol fatty acid ester such as polyoxyethylene sorbitol tetrastearate or polyoxyethylene sorbitol tetraoleate; a polyoxyethylene glycerin fatty acid ester such as polyoxyethylene glyceryl monostearate; a polyethylene glycol fatty acid ester such as polyethylene glycol distearate; a polyoxyethylene alkyl ether such as polyoxyethylene lauryl ether; a polyoxyethylene polyoxypropylene alkyl ether such as polyoxyethylene polyoxypropylene glycol ether, polyoxyethylene polyoxypropylene propyl ether, or polyoxyethylene polyoxypropylene cetyl ether; a polyoxyethylene alkylphenyl ether such as polyoxyethylene nonylphenyl ether; a polyoxyethylene hardened castor oil such as polyoxyethylene castor oil, polyoxyethylene hardened castor oil (polyoxyethylene hydrogenated castor oil); a polyoxyethylene beeswax derivative such as polyoxyethylene sorbitol beeswax; a polyoxyethylene lanolin derivative such as polyoxyethylene lanolin; a surfactant having HLB 6 to 18 such as a polyoxyethylene fatty acid amide (for example, polyoxyethylene stearamide); an anionic surfactant such as an alkyl sulfate having 8 to 18 carbon atoms (for example, sodium cetyl sulfate, sodium lauryl sulfate, or sodium oleyl sulfate); a polyoxyethylene alkyl ether sulfate having the average number of additional moles of 2 to 4 of ethylene oxide and 8 to 18 carbon atoms at an alkyl group (for example, sodium polyoxyethylene lauryl sulfate); an alkyl benzene sulfonate having 8 to 18 carbon atoms at an alkyl group such as sodium lauryl benzene sulfonate; an alkyl sulfosuccinate having 8 to 18 carbon atoms at an alkyl group such as sodium lauryl sulfosuccinate; a natural surfactant such as lecithin or glycerophospholipid; a sphingophospholipid such as sphingomyelin; and a saccharose fatty acid ester of a fatty acid ester having 8 to 18 carbon atoms. Those surfactants were added, alone or in combination with two kinds or more, to an ejecting liquid (liquid compositions) of the present invention.

Preferable surfactants include polyoxyethylene sorbitan fatty acid ester, N-acylamino acid, and fatty acid salts of amino acids, and particularly preferable surfactants include polyoxyethylene 20 sorbitan monolaurate, polyoxyethylene (4) sorbitanmonooleate, N-coconut oil fatty acid glycine, N-coconut oil fatty acid glutamic acid, N-lauroyl sarcosine, and arginine coconut oil fatty acid salt. Of those, most preferable surfactants include polyoxyethylene 20 sorbitan monolaurate, polyoxyethylene 20 sorbitan monooleate, N-lauroyl sarcosine, and arginine coconut oil fatty acid salt. In addition, those preferable for pulmonary inhalation include polyoxyethylene 20 sorbitan monolaurate and polyoxyethylene 20 sorbitan monooleate.

The surfactant may be added at a concentration of, for example, 0.001 to 20% by weight for insulin, although the concentration depends on the co-existing protein or the like. In addition, the surfactant is preferably added at a concentration of 0.1 to 1.0 part by weight with respect to one part by weight of the compound having a guanidine group.

In the present invention, the protein may be mixed with amino acids and the surfactant in advance or may be mixed just before the ejection. It is preferable to mix them uniformly before the ejection.

In the embodiments of the present invention, for removing microbial effects, an antimicrobial agent, a germicidal agent, and an antiseptic agent may be added. Examples of those agents include: phenolic derivatives such as phenol, cresol, and anisole; quaternary ammonium salts such as benzalkonium chloride and benzatonium chloride; benzoic acids such as benzoic acid and paraoxybenzoic acid ester; and sorbic acid.

In some embodiments of the present invention, for elevating physical stability in conservation, any one of oil, glycerin, ethanol, urea, cellulose, polyethylene glycol, and alginate may be added. In addition, for elevating chemical stability, ascorbic acid, citric acid, cyclodextrin, tocopherol, or any other anti-oxidizing agent may be added.

Any buffer may be added to adjust the pH of the ejection liquid. Examples of the buffer, which may be used, include ascorbic acid, citric acid, diluted hydrochloric acid, and diluted sodium hydroxide, and also include other buffers such as sodium hydrogenphosphate, sodium dihydrogen phosphate, potassium hydrogenphosphate, potassium dihydrogen phosphate, PBS, HEPES, and Tris.

Aminoethylsulfonic acid, potassium chloride, sodium chloride, glycerin, or sodium bicarbonate may be added as an isotonizing agent.

Any one of saccharides such as glucose and sorbitol, sweetening agents such as aspartame, menthol, and various aromatics may be added as a flavoring agent.

When the above ejection liquid is used for the production of a biochip or biosensor or for screening of protein, a system, which is almost the same as an inkjet printer commercially available at present, can be used.

Figure 2:
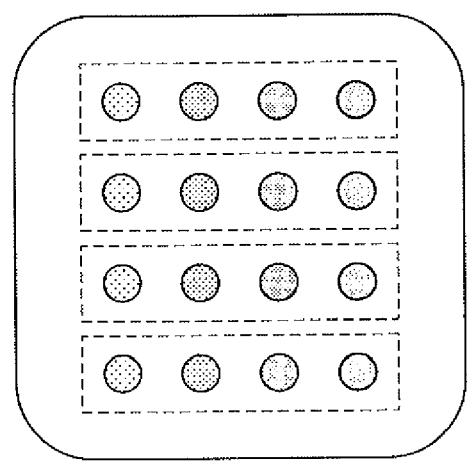
Figure 3:
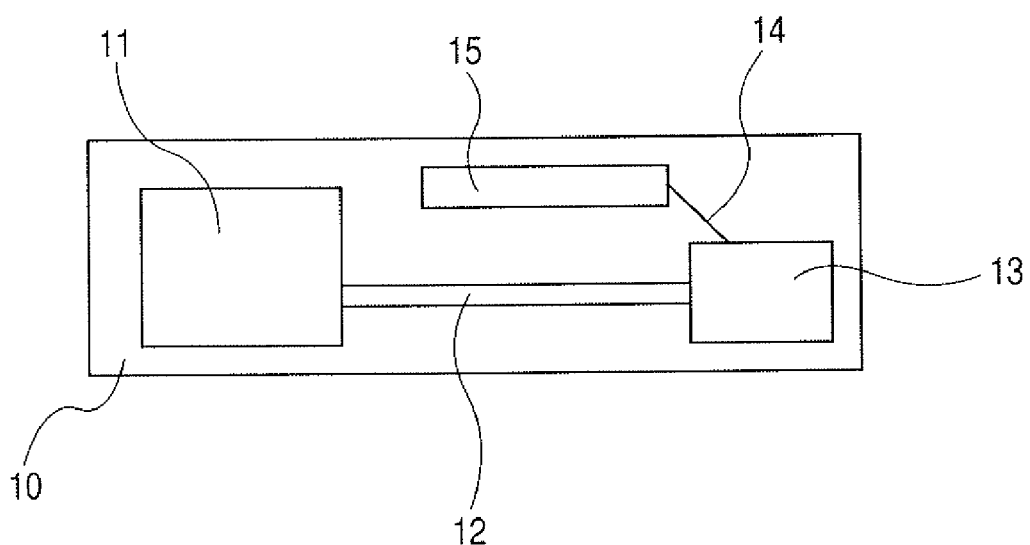
Figure 4:
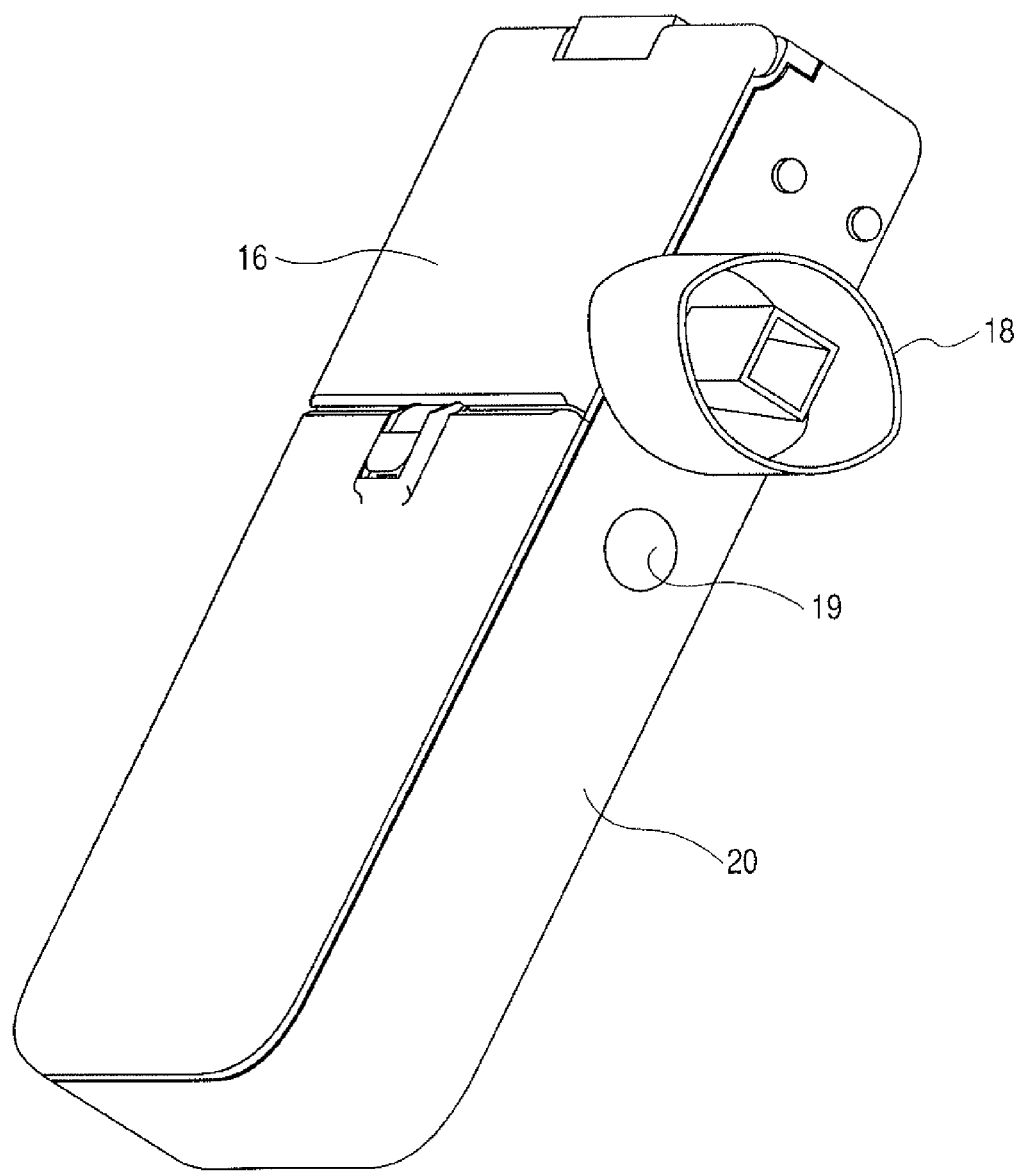
Figure 5:
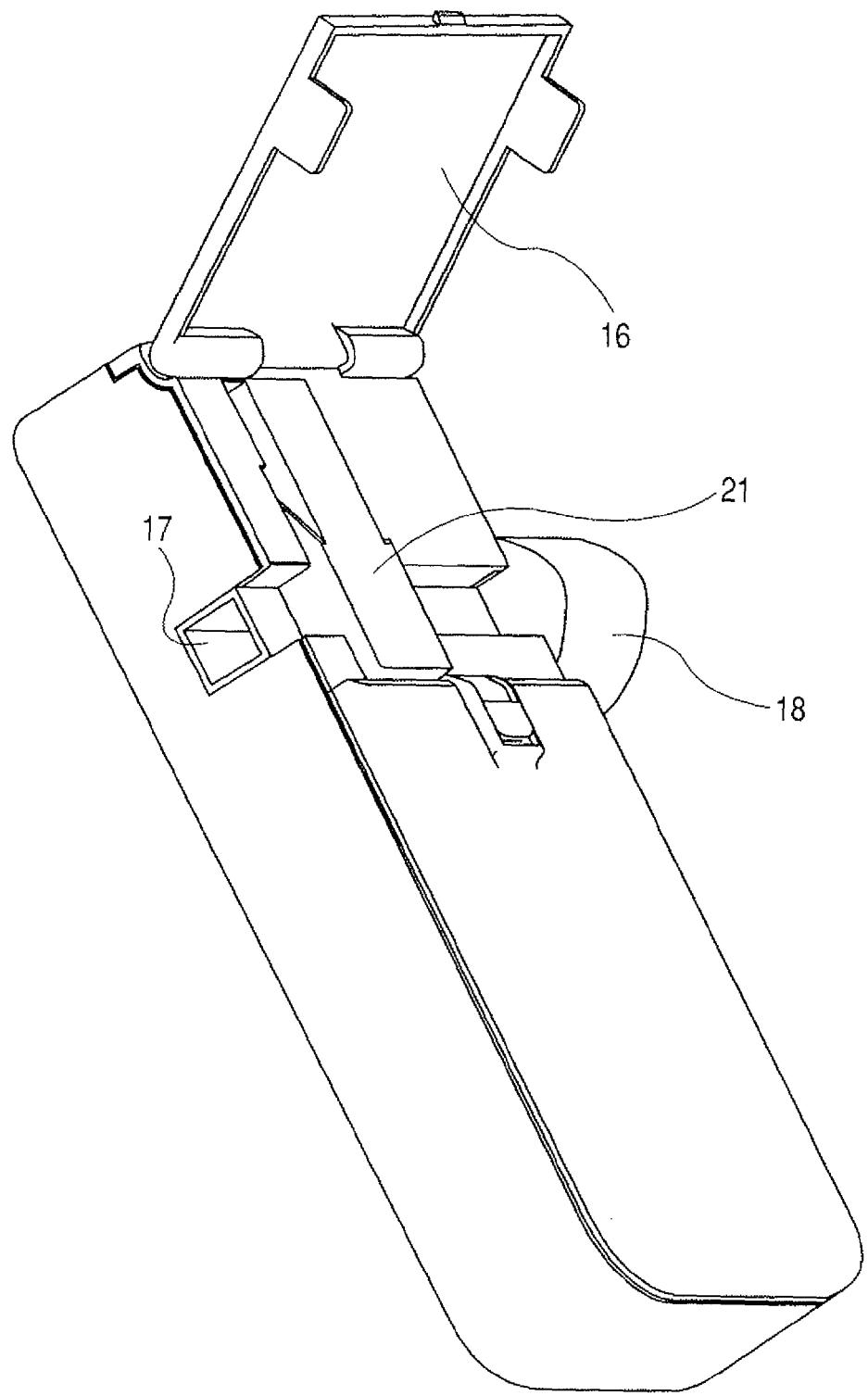
FIG. 5 is a perspective diagram of a state in which an access cover is opened in FIG. 4.
Figure 6:
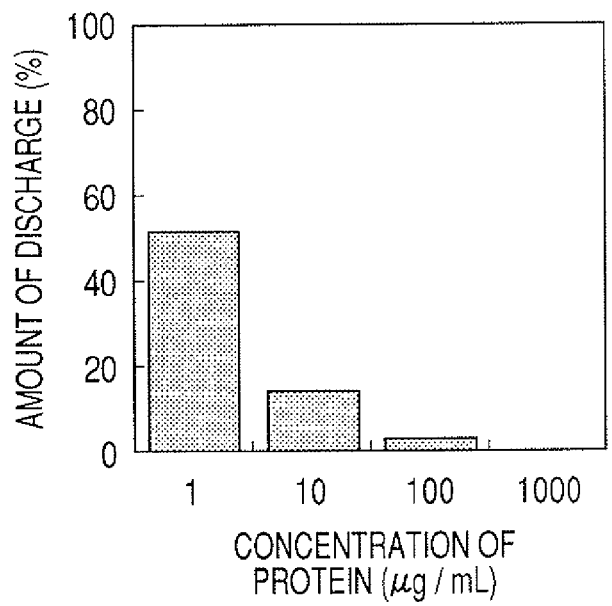
FIG. 6 is a graphical representation of the ejection amount of an albumin solution when it is ejected using a bubble jet method.

The details will be described with reference to FIG. 1. An ejection liquid is filled in a nozzle of an inkjet head 3 via a tank 1. The ejection liquid 4 is ejected by driving an inkjet head under the control of a drive controller 6 onto a substrate 5 suitable for intended purpose to form a pattern thereon, while the distance between the substrate and the nozzle surface of the inkjet head is kept constant. Reference numeral 2 denotes a liquid flow path. The pattern may be formed on the substrate by discharging an image pattern. Alternatively, however, it is preferable to form a pattern in which spots are not linked with each other as shown in FIG. 2.

In addition, a solution containing a test substance is ejected with the same pattern on the substrate to initiate a reaction between the substrate and the test substance efficiently, or may be ejected with variations in concentration by causing variation in ejection amount of the test sample.

When the above ejection liquid is used for pulmonary inhalation, an indispensable part is a device capable of discharging the dosage formulation of the present invention as droplets having a small particle size distribution of 1 to 5 μm. A head part for discharging the droplets is a detachable cartridge unit. The cartridge unit includes the following parts. It will be described with reference to FIG. 3. A cartridge 10 has a tank 11 in which a drug is filled, a liquid flow path 12 for supplying the drug to an evaporation point located adjacent to an orifice (ejection orifice), a head part (liquid-discharging part) 13 for discharging the ejection liquid, and wiring 14 including an electric connection part 15 with a controller. The details of the head part 13 correspond to a liquid-ejection head described in Japanese Patent Application Laid-Open No. 2003-154665.

An inhaler to be provided as an ejection controller is designed to be carried and possessed by a user, and also capable of discharging a constant amount of the drug as droplets having a uniform particle size, thereby allowing the user to inhale the drug.

Referring now to FIGS. 4 and 5, the schematic configuration of the inhaler to be used in the present invention will be described.

FIG. 4 is a perspective diagram showing an external view of the inhaler, where reference numeral 20 denotes the body of the inhaler and 16 denotes an access cover, and the body and the cover form a housing. Reference numeral 19 denotes an electric source. In FIG. 5, there is shown the access cover 16 being opened. When the access cover 16 is opened, a head cartridge unit 21 and a mouthpiece 18 can be seen. When a user performs an inhalation movement, the air can enter the mouthpiece 18 through an air intake 17 and be then mixed with a drug ejected from an ejection orifice formed in the head part of the head cartridge unit 21, followed by moving toward the outlet of the mouthpiece in the form of allowing a person to sputter. The user puts the tip of the mouthpiece into the mouth and then holds it by teeth, followed by drawing in a breath. Thus, the drug solution ejected as droplets from the liquid ejection part of the head cartridge unit can be inhaled effectively.

Furthermore, the head cartridge unit 21 can be designed so as to be removably attached on the inhaler if necessary.

By adopting the configuration shown in FIGS. 4 and 5, microdroplets formed can naturally reach the throat, and the inside of the trachea, of the subject to which they are to be administered with inspired air. Therefore, the amount of the nebulized liquid (the dosage of active ingredient) can be independently controlled without depending on the volume of air to be inhaled.

EXAMPLES

Before carrying out the example, for more understanding the difficulty in ejection of a protein solution, the ejection amounts are represented when only the protein is ejected by the thermal inkjet method. The protein solution used is albumin dissolved in PBS and then ejected at each concentration using a thermal inkjet printer (trade name: PIXUS 950i, manufactured by Canon Inc.) which is a remodeled product for collecting the solution. In contrast, the ejection amounts of the respective albumin solutions are represented with respect to the amount of PBS buffer similarly ejected, which is defined as 100%. The results are shown in FIG. 6.

The stability of ejection is not complete even when the concentration of albumin is as small as 1 μg/ml. The ejection becomes gradually more difficult as the concentration of the protein increases. When the present invention is carried out, droplets to be ejected must have smaller sizes, so it may be difficult to eject a protein solution.

Hereinafter, the present invention will be described in more detail with reference to the examples. These examples are concrete examples being illustrated for more profound understanding, so that the present invention is not restricted by these concrete examples at all. Here, "%" stands for "% by weight".

Examples 1 to 8 and Comparative Examples 1 to 30

(Preparing Droplets of Protein Solution with Thermal Inkjet Method)

The procedure of preparing an ejection liquid was carried out such that albumin was previously dissolved in PBS buffer at an appropriate concentration and then stirred while a compound having a guanidine group was added, followed by adjusting the concentrations of the respective substances to predetermined constant levels using PBS buffer.

Previously, the head cartridge having a nozzle diameter of 3 μm to be used for an ejection experiment was filled with a 30% ethanol aqueous solution. Subsequently, a laser diffraction type measuring device for particle size distribution (SprayTech, manufactured by Malvern Co., Ltd.) was used for measuring particle size and particle size distribution to detect droplets having a particle size distribution sharply found at 3 μm.

The above head cartridge having a nozzle diameter of 3 μm was filled with an ejection liquid prepared in advance and then connected to an ejection controller, followed by carrying out ejection for 1 second at a frequency of 20 kHz at a voltage of 12V with an interval of 3 seconds to the subsequent ejection. This procedure was repeated 50 times, followed by visually observing whether the ejection occurred. The case where ejection occurred 50 times or more was evaluated as ○, the case where ejection occurred 15 times or more but less than 50 times was evaluated as Δ, and the case where ejection occurred less than 15 times evaluated as ×. In addition, HPLC assay was carried out on the ejection liquid before and after the ejection thereof (assay conditions: device; JASCO Corp., Column; YMC-Pack Diol-200, 500×8.0 mm ID, Eluent; 0.1 M $KH_2PO_4$-$K_2HPO_4$ (pH 7.0) containing 0.2 M NaCL, Flow rate; 0.7 ml/min, Temperature; 25° C., Detection, UV at 215 nm) to observe a change in composition of the ejection liquid.

As comparative examples, ejection liquids were prepared using pure water, various protein solutions, and substances other than those used for the present invention and an experiment was then carried out such that the respective liquids were ejected by the same way as that of the examples. Here, the formulations studied for the examples and comparative examples and the results thereof were listed in Table 1 below.

TABLE 1

| | Protein | Protein concentration (mg/mL) | Additive | Additive concentration (mg/mL) | Ejection ability |
|---|---|---|---|---|---|
| Example 1 | Albumin | 1.0 | Guanidine hydrochloride | 200 | ○ |

TABLE 1-continued

| | Protein | Protein concentration (mg/mL) | Additive | Additive concentration (mg/mL) | Ejection ability |
|---|---|---|---|---|---|
| Example 2 | Albumin | 1.0 | N-ethyl guanidine hydrochloride | 200 | ○ |
| Example 3 | Albumin | 1.0 | N,N'-dimethyl biguanide hydrochloride | 200 | ○ |
| Example 4 | Albumin | 1.0 | Arginine | 100 | ○ |
| Example 5 | Albumin | 1.0 | Homoarginine | 100 | ○ |
| Example 6 | Albumin | 1.0 | 2-amino-4-guanidino-butyl acid | 100 | ○ |
| Example 7 | Albumin | 1.0 | Arginine ethylester | 100 | ○ |
| Example 8 | Albumin | 1.0 | Nα-acetyl arginine hydrochloride | 100 | ○ |
| Comparative Example 1 | Pure water | 0 | — | — | ○ |
| Comparative Example 2 | Glucagon | 1.0 | Unavailable | — | x |
| Comparative Example 3 | GLP-1 | 1.0 | Unavailable | — | x |
| Comparative Example 4 | G-CSF | 1.0 | Unavailable | — | x |
| Comparative Example 5 | EPO | 1.0 | Unavailable | — | x |
| Comparative Example 6 | INF α | 1.0 | Unavailable | — | x |
| Comparative Example 7 | INF γ | 1.0 | Unavailable | — | x |
| Comparative Example 8 | Calcitonin | 1.0 | Unavailable | — | x |
| Comparative Example 9 | IL-2 | 1.0 | Unavailable | — | x |
| Comparative Example 10 | IL-6 | 1.0 | Unavailable | — | x |
| Comparative Example 11 | TNF α | 1.0 | Unavailable | — | x |
| Comparative Example 12 | Albumin | 1.0 | Unavailable | — | x |
| Comparative Example 13 | Insulin | 1.0 | Unavailable | — | x |
| Comparative Example 14 | GOT | 0.1 | Unavailable | — | x |
| Comparative Example 15 | γ-GGT | 0.1 | Unavailable | — | x |
| Comparative Example 16 | LDH | 0.1 | Unavailable | — | x |
| Comparative Example 17 | ALP | 0.1 | Unavailable | — | x |
| Comparative Example 18 | Albumin | 1.0 | Glycerin | 200 | x |
| Comparative Example 19 | Albumin | 1.0 | Sucrose | 200 | x |
| Comparative Example 20 | Albumin | 1.0 | Glycine | 200 | x |
| Comparative Example 21 | Albumin | 1.0 | Lysine | 200 | x |
| Comparative Example 22 | Albumin | 1.0 | PEG6000 | 150 | x |
| Comparative Example 23 | Albumin | 1.0 | Polyoxyethylene lauryl ether | 50 | x |
| Comparative Example 24 | Albumin | 1.0 | Tween80 | 50 | Δ |
| Comparative Example 25 | Albumin | 1.0 | Tween80 | 100 | x |
| Comparative Example 26 | Albumin | 1.0 | PEG6000 | 150 | x |
| Comparative Example 27 | Albumin | 1.0 | Urea | 100 | x |
| Comparative Example 28 | Albumin | 1.0 | Citrulline | 200 | x |
| Comparative Example 29 | Insulin | 1.0 | Carnitine | 100 | x |
| Comparative Example 30 | Insulin | 10 | PEG6000 + Tween80 | 60 + 1.0 | x |

Pure water of Comparative Example 1 was ejected stably without a break because of no protein in the pure water. However, each of Comparative Examples 2 to 23 and 25 to 30 which contained protein could not be ejected at all or was ejected little without depending on the kind of protein and the presence or absence of additives. When the surfactant Tween 80 was added as represented in Comparative Example 14, the ejection occurred to some extent but resulted in poor stability. In addition, when the concentration of Tween 80 added was increased, in contrast, no ejection was observed at all. On the other hand, in each of Examples 1 to 8, the ejection was carried out normally and stabilized. As a result of HPLC analysis, in each of Examples 1 to 8, there were no changes in peak position and in peak area before and after the ejection and also no change was recognized in the liquid composition.

Examples 9 to 31

(Effects on Various Proteins and Concentrations of Additives)

Next, arginine was chosen as a compound having a guanidine group and then added at certain concentrations to various proteins. Those ejection liquids were evaluated by the same way as that of Example 1 under the same ejection experiment. Here, the formulations studied in the examples and the results obtained were listed in Table 2 below.

TABLE 2

| | Protein | Protein concentration (mg/mL) | Arginine concentration (mg/mL) | Ejection ability |
|---|---|---|---|---|
| Example 9 | Insulin | 1.0 | 10 | Δ |
| Example 10 | Insulin | 1.0 | 50 | ○ |
| Example 11 | Insulin | 5.0 | 100 | ○ |
| Example 12 | Insulin | 10 | 200 | ○ |
| Example 13 | Insulin | 10 | 100 | ○ |
| Example 14 | Albumin | 1.0 | 50 | Δ |
| Example 15 | Albumin | 1.0 | 100 | ○ |
| Example 16 | Albumin | 3.0 | 100 | Δ |
| Example 17 | Albumin | 3.0 | 200 | ○ |
| Example 18 | GOT | 0.1 | 50 | ○ |
| Example 19 | γ-GTP | 0.1 | 50 | ○ |
| Example 20 | LDH | 0.1 | 50 | ○ |
| Example 21 | ALP | 0.1 | 50 | ○ |
| Example 22 | Glucagon | 1.0 | 50 | ○ |
| Example 23 | GLP-1 | 1.0 | 50 | ○ |
| Example 24 | G-CSF | 1.0 | 50 | ○ |
| Example 25 | EPO | 1.0 | 50 | ○ |
| Example 26 | INF α | 1.0 | 50 | ○ |
| Example 27 | INF γ | 1.0 | 50 | ○ |
| Example 28 | Calcitonin | 1.0 | 50 | ○ |
| Example 29 | IL-2 | 0.1 | 50 | ○ |
| Example 30 | IL-6 | 0.1 | 50 | ○ |
| Example 31 | TNF α | 0.1 | 50 | ○ |

Due to the concentrations and types of proteins, in spite of difference in required addition concentrations, the addition of arginine permitted normal ejection of the respective proteins with the thermal inkjet method. Therefore, it was confirmed that arginine can effect on a wide variety of proteins. In addition, HPLC assay was conducted on the examples in which normal ejection was observed. As a result, there was no change in peak chart before and after the ejection and no change in liquid composition was then confirmed.

Example 32

(Confirmation of Pharmacological Activity)

Figure 7:
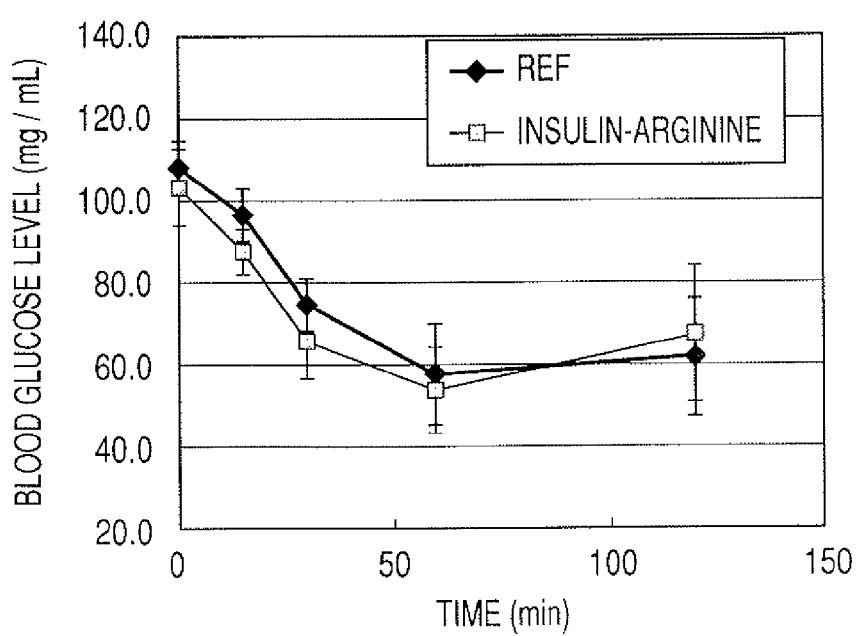
FIG. 7 is a graphical representation of the time cause of blood glucose levels in rats with the administration of insulin.

In the composition shown in Example 10, the pharmacological activity of the composition was investigated before and after the ejection. As an experiment, 8-week male Wistar rats with a body weight of about 250 g were fasted for one day and then anesthetized with Nembutal, followed by collecting blood from a tail vein. This state was decided as a base line. After that, a solution having the composition of Example 10 was ejected by the thermal inkjet method and collected, and was then hypodermically injected so as to be 1.6 U/kg, followed by collecting blood from the tail vein of the animal at 15, 30, 60, and 120 minutes after the administration. The collected blood was centrifuged and the resulting serum was then subjected to measurement of blood glucose levels (6 animals/group). An insulin solution in the absence of any additive, which had not been ejected by the thermal inkjet method, was tested similarly and then provided as a control. The solution-administered samples of Example 10, which had been ejected by the thermal inkjet method, were investigated whether variations in the pharmacological activities were present or not owing to variations in blood glucose levels. The results are shown in FIG. 7.

As a result of experiment, the blood glucose levels of rats administered with insulin reduced immediately. Therefore, it was observed that insulin had a depression effect on blood glucose levels. In contract, it was observed that the formulation of Example 10, which had been ejected by the thermal inkjet method, also showed a similar depression effect on blood glucose levels. As for the depression effect on blood glucose levels, no significant difference with the comparative example was found in each observation point. It was confirmed that, even after inkjet-discharging of the formulation of Example 10, the activity thereof had been maintained.

Example 33

(Efficiency of Ejection)

A solution containing insulin of 1.0 mg/ml in concentration was ejected by the thermal inkjet method and the amount of ejection was then evaluated with respect to the presence or absence of an additive, confirming the reproducibility thereof.

Figure 8:
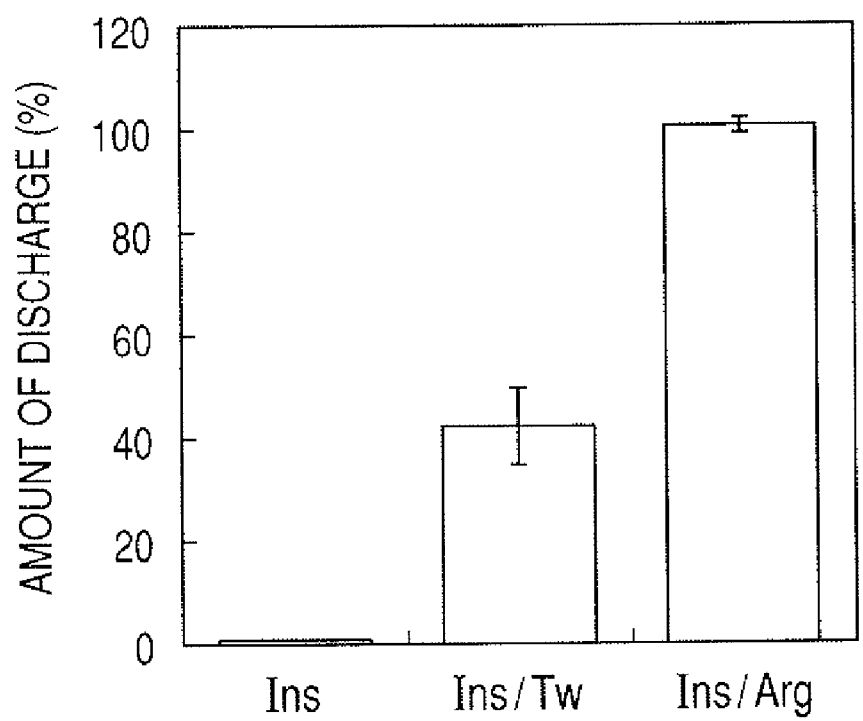
FIG. 8 is a graphical representation of the ejection amount of an insulin solution when it is ejected using a bubble jet method.

The ejected solutions were: a solution (Ins/Arg) prepared by adding 1.0 mg/ml of arginine to 1.0 mg/ml of an insulin solution; a solution (Ins/Tw) prepared by adding 1.0 mg/ml of Tween 80 to 1.0 mg/ml of an insulin solution; and a solution containing 1.0 mg/ml of insulin only. Those solutions were ejected using a bubble jet printer (trade name: PIXUS 950i, manufactured by Canon Inc.) which was a remodeled product for collecting the solution. The ejection amount of pure water similarly ejected was defined as 100%. FIG. 8 shows a graph of the ejection amount of each solution. Experiment was conducted on each solution 5 times. The average and the standard deviation were shown.

The amount of the solution added with insulin only was little or nothing, and the efficiency of ejection was very low. The amount of the solution added with insulin in Tween 80 was about 40% with reference to that of pure water. In this case, however, there was no reproducibility because of variations in ejection amounts. On the other hand, the solution added with insulin in arginine showed almost the same ejection amount as that of the ejected pure water and also showed high reproducibility. When ejected similarly, the ejection amount of the solution added with insulin in arginine was 100 times or more as high as that of the solution added with insulin only. In addition, it was about 2.5 times as high as the ejection amount of the solution added with insulin in Tween 80. Therefore, it was confirmed that the ejection efficiency increased very much.

Examples 34 to 52

(Synergistic Effect of Compound having Guanidine group With Surfactant)

Ejection liquids were prepared such that a surfactant was added to a solution added with a compound having a guanidine group in protein. The resulting ejection liquids were evaluated by the same ejection experiment as that of Example 1. Here, formulations studied in the examples and the results obtained were listed in Table 3 below.

TABLE 3

| | Protein | Protein concentration (mg/mL) | Arginine concentration (mg/mL) | Tween 80 concentration (mg/mL) | Ejection ability |
|---|---|---|---|---|---|
| Example 34 | Albumin | 1.0 | 10 | 10 | ○ |
| Example 35 | Albumin | 5.0 | 50 | 20 | ○ |
| Example 36 | Albumin | 10 | 200 | 10 | ○ |
| Example 37 | Insulin | 10 | 50 | 5.0 | ○ |
| Example 38 | Insulin | 40 | 200 | 10 | ○ |
| Example 39 | GOT | 0.1 | 5.0 | 5.0 | ○ |
| Example 40 | γ-GTP | 0.1 | 5.0 | 5.0 | ○ |
| Example 41 | LDH | 0.1 | 5.0 | 5.0 | ○ |
| Example 42 | ALP | 0.1 | 5.0 | 5.0 | ○ |
| Example 43 | Glucagon | 1.0 | 10 | 10 | ○ |
| Example 44 | GLP-1 | 1.0 | 5.0 | 5.0 | ○ |
| Example 45 | G-CSF | 1.0 | 10 | 10 | ○ |
| Example 46 | EPO | 1.0 | 5.0 | 5.0 | ○ |
| Example 47 | INF α | 1.0 | 10 | 10 | ○ |
| Example 48 | INF γ | 1.0 | 10 | 10 | ○ |
| Example 49 | Calcitonin | 1.0 | 10 | 10 | ○ |
| Example 50 | IL-2 | 0.1 | 5.0 | 5.0 | ○ |
| Example 51 | IL-6 | 0.1 | 5.0 | 5.0 | ○ |
| Example 52 | TNF α | 0.1 | 5.0 | 5.0 | ○ |

When arginine and Tween 80 were added at the same time, it was possible to eject the protein solution at an extremely smaller concentration than that of one added with arginine only. In addition, it was ejected at a concentration at which the solution added with arginine only could not be ejected. Besides, the amounts of the additives were largely decreased as a whole. Furthermore, it became possible to eject the high-concentration protein solution with the synergistic effect. As a result of carrying out HPLC assay on each of Examples 19 to 24, there was no change in peak chart before and after the ejection and no change was found in the liquid composition.

Example 53

(Manufacture of Antibody Chip Using Inject Printer and Sensing)

Figure 9:
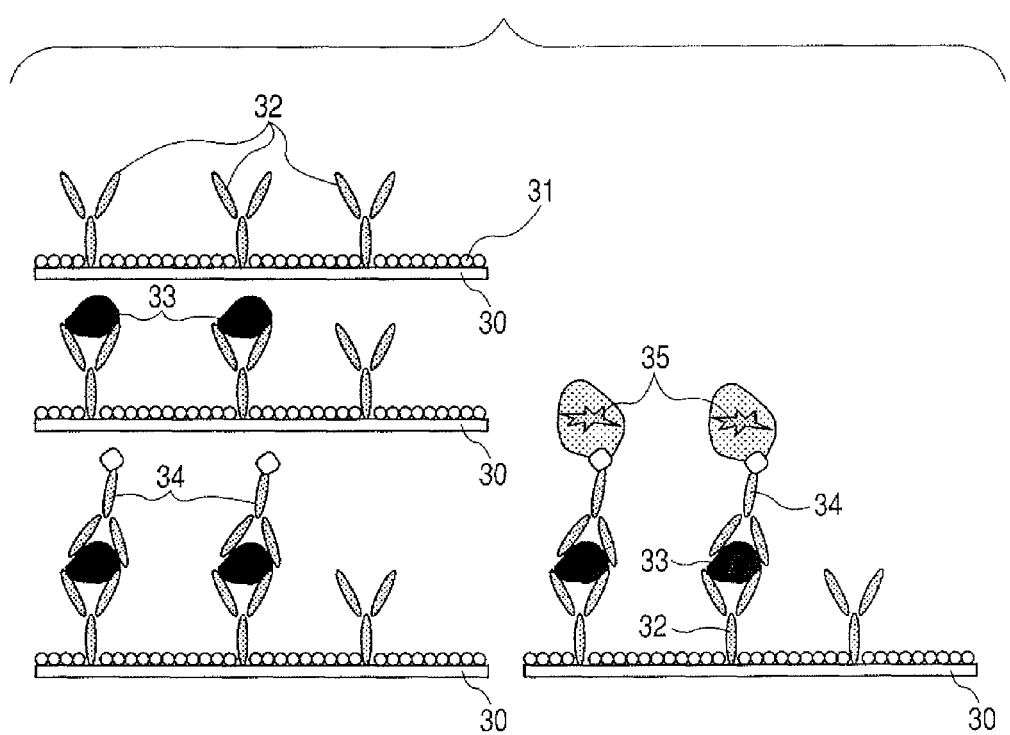
FIG. 9 is a diagram of a model of the experiment method of an example.

FIG. 9 shows a model of this example. In FIG. 9, reference numeral 30 is a substrate, 31 is a masking agent, and 32 is a substance (such as protein or peptide) to react with a test substance in a specific manner, 33 is the test substance, 34 is a substance specific to the test substance, and 35 is a label, which are schematically represented.

Each of human IL2 monoclonal antibody, human IL4 monoclonal antibody, and human IL6 monoclonal antibody was prepared at a concentration of 0.1 to 500 μg/ml in PBS. Here, L-arginine was added so as to become 1% (w/w) to prepare an ejection liquid. The resulting solution was filled in a head of an inkjet printer (trade name: PIXUS 950i, manufactured by Canon Inc.) and then ejected on a poly-L-Lysine-coated slide glass.

The glass after ejection was incubated at 4° C., and the incubated glass was then masked with 1% BSA. After masking, the glass was washed very well and then provided as an antibody-chip substrate.

The chip and test substances, recombinants IL2, IL4, and IL6, each 1 μg/ml, were prepared in PBS together with 1.0% L-arginine (w/w), 0.5% Tween 20 (w/w), and 0.1% BSA (w/w), respectively. The solution was filled in the head of the inkjet printer (trade name: PIXUS 950i, manufactured by Canon Inc.) and then ejected on the above substrate with the same patterns. After discharging, a cover glass was placed on the substrate and allowed to react at 4° C. After the reaction, the resultant was washed very well and then dried.

Subsequently, the substrate was subjected to a reaction with a substance which could be specifically attached to the sample, and the substance was then labeled. Each of antibody solutions which were labeled with biotin as substances specifically attached to the sample (biotinylated human IL2 monoclonal antibody, biotinylated human IL4 monoclonal antibody, and biotinylated human IL6 monoclonal antibody) was prepared in PBS so as to become a final concentration of 1 μg/ml together with 1.0% L-arginine (w/w), 0.5% Tween 20 (w/w), and 0.1% BSA (w/w), followed by being filled in the head of the inkjet printer (trade name: PIXUS 950i, manufactured by Canon Inc.) and then ejected on the above substrate with the same patterns. After discharging, a cover glass was placed on the substrate and allowed to react at 4° C. After the reaction, the resultant was washed very well and then dried.

For labeling, 10 μg/ml of Cy3-labeled streptavidine was prepared in PBS so as to become a final concentration of 1.0% L-arginine (w/w), 0.5% Tween 20 (w/w), and 0.1% BSA (w/w), followed by being filled in the head of the inkjet printer (trade name: PIXUS 950i, manufactured by Canon Inc.) and then ejected on the above substrate with the same patterns. After discharging, a cover glass was placed on the substrate and allowed to react at 4° C. After the reaction, the resultant was washed very well and then dried.

After that, excitation light was applied to the post-reaction substrate and the level of a fluorescence signal was then measured with respect to the emission of Cy3 using a fluorescence scanner on which a filter having a transmission wavelength of 532 nm had been placed. Consequently, fluorescence signals depending on the types and concentrations of the samples were detected.

This application claims priority from Japanese Patent Application Nos. 2004-279864 filed Sep. 27, 2004 and 2005-252154 filed Aug. 31, 2005, which are hereby incorporated by reference herein.

The invention claimed is:

1. A method of using a compound having a guanidine group to produce an ejection liquid to be ejected by a thermal inkjet method, the ejection liquid comprising (a) the compound having a guanidine group and (b) at least one selected from proteins and peptides, wherein the method comprises a production method of producing the ejection liquid, the production method comprising the steps of:
    dissolving at least one selected from proteins and peptides into a liquid medium to form a solution;
    adding the compound having a guanidine group to the solution; and
    co-adding at least one surfactant selected from the group consisting of N-lauroyl sarcosine and arginine coconut oil fatty acid salt,
    wherein the compound having a guanidine group is a compound selected from the group consisting of:
    (a) a compound represented by the general formula (1):

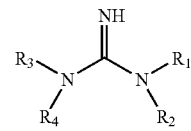

wherein $R_1$, $R_2$ and $R_3$ is independently a hydrogen atom, and $R_4$ is a hydrogen atom, or a straight or branched alkyl group having 1-6 carbon atoms;
    (b) a compound represented by the general formula (2):

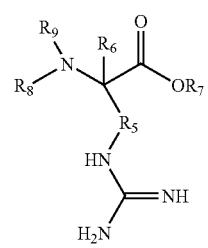

wherein $R_5$ is a straight alkyl group having 1-6 carbon atoms, $R_6$ is a hydrogen atom, $R_7$ is a hydrogen atom, or a straight or branched alkyl group having 1-6 carbon atoms, $R_8$ is a hydrogen atom, and $R_9$ is a hydrogen atom, or a straight or branched acyl group having 1-6 carbon atoms;
    (c) N,N'-dimethyl biguanide; and
    (d) salts thereof.

2. The method of using a compound according to claim 1, wherein the surfactant is N-lauroyl sarcosine.

3. The method of using a compound according to claim 1, wherein the surfactant is arginine coconut oil fatty acid salt.

* * * * *